(12) United States Patent
Donaldson et al.

(10) Patent No.: US 10,041,893 B2
(45) Date of Patent: Aug. 7, 2018

(54) METHODS AND SYSTEMS FOR IDENTIFYING HYDROCARBON FLUID TRANSITION CHARACTERISTICS USING NUCLEAR MAGNETIC RESONANCE

(71) Applicant: SCHLUMBERGER TECHNOLOGY CORPORATION, Sugar Land, TX (US)

(72) Inventors: Marcus Hofheins Donaldson, Somerville, MA (US); Denise Freed, Newton Highlands, MA (US); Martin Hurlimann, Newton, MA (US); Yi-Qiao Song, Newton Center, MA (US); Lalitha Venkataramanan, Lexington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 696 days.

(21) Appl. No.: 14/581,307

(22) Filed: Dec. 23, 2014

(65) Prior Publication Data
US 2016/0178545 A1 Jun. 23, 2016

(51) Int. Cl.
*G01V 3/00* (2006.01)
*G01N 24/08* (2006.01)
(52) U.S. Cl.
CPC .................. *G01N 24/081* (2013.01)
(58) Field of Classification Search
USPC ....................................................... 324/303
See application file for complete search history.

(56) References Cited

U.S. PATENT DOCUMENTS 6,041,017 A * 3/2000 Goldsberry .............. G01V 1/44
367/37
6,172,720 B1 * 1/2001 Khan ..................... C09K 19/54
252/299.5
(Continued)

FOREIGN PATENT DOCUMENTS

WO 2009025688 A1 2/2009

OTHER PUBLICATIONS

Adams, et al., "Bayesian Online Changepoint Detection", Technical Report, University of Cambridge, Cambridge, UK, 2007, 7 pages.
(Continued)

*Primary Examiner* — Rodney Fuller (57) ABSTRACT

Methods are provided for identifying one or more transition characteristics in a hydrocarbon fluid such as asphaltene onset pressure (AOP), bubble point or dew point. A transition characteristic is determined by subjecting the fluid to different pressures or temperatures, conducting NMR tests at the different pressures or temperatures to obtain signals, processing the signals to obtain values of a function of an NMR parameter as a function of pressure or temperature, and analyzing the values to find a discontinuity that identifies the transition characteristic. In embodiments, the NMR parameters may include at least one of a relaxation parameter such as $T_2$ or a $T_1$-$T_2$ ratio, a diffusion parameter and an initial magnetization parameter. In embodiments, dual linear fitting, Bayesian change point detection algorithms, and instantaneous slope analysis may be utilized to analyze the values in order to find a discontinuity.

24 Claims, 11 Drawing Sheets

(56) References Cited

U.S. PATENT DOCUMENTS

| | | | | |
|---|---|---|---|---|
| 6,223,588 B1* | 5/2001 | Burgass | ............... | G01N 25/085 |
| | | | | 73/19.01 |
| 6,346,813 B1* | 2/2002 | Kleinberg | ............ | G01N 24/081 |
| | | | | 324/303 |
| 7,637,151 B2* | 12/2009 | Raghuraman | ...... | G01N 33/2823 |
| | | | | 250/255 |
| 2002/0194907 A1 | 12/2002 | Bostrom et al. | | |
| 2003/0128032 A1 | 7/2003 | Heaton et al. | | |
| 2005/0242807 A1 | 11/2005 | Freedman | | |
| 2005/0270023 A1* | 12/2005 | Freedman | ............ | G01N 24/081 |
| | | | | 324/303 |
| 2009/0256562 A1* | 10/2009 | Gao | ........................ | G01N 24/08 |
| | | | | 324/308 |
| 2011/0094801 A1* | 4/2011 | Buchanan | ............... | E21B 49/06 |
| | | | | 175/249 |
| 2011/0218736 A1* | 9/2011 | Pelletier | ................ | E21B 49/081 |
| | | | | 702/12 |
| 2012/0296617 A1* | 11/2012 | Zuo | ........................ | E21B 47/10 |
| | | | | 703/10 |
| 2013/0002246 A1 | 1/2013 | Venkataramanan et al. | | |

OTHER PUBLICATIONS

Freedman, et al., "A compact high-performance low-field NMR apparatus for measurements on fluids at very high pressures and temperatures", Rev. Sci. Instrum. 85, 025102, 2014, 11 pages.
International Search Report and Written Opinion for corresponding PCT Application No. PCT/US2015/064371, dated Mar. 31, 2016, 15 pages.

* cited by examiner

METHODS AND SYSTEMS FOR IDENTIFYING HYDROCARBON FLUID TRANSITION CHARACTERISTICS USING NUCLEAR MAGNETIC RESONANCE

TECHNICAL FIELD

The subject disclosure relates to methods for investigating hydrocarbon fluids using nuclear magnetic resonance (NMR). More particularly, the subject disclosure relates to methods for identifying one or more transition characteristics in a hydrocarbon fluid using NMR measurements obtained while subjecting the hydrocarbon fluid to different pressures.

BACKGROUND

Nuclear magnetic resonance (NMR) is a useful tool in investigating the properties of a sample. More specifically, NMR tools are used in laboratories as well as in boreholes traversing earth formations in order to investigate the properties of fluids and rock samples. The NMR tools used downhole are able to generate fields that result in signals indicating the presence of water and hydrocarbons in the formation.

One frequently used NMR technique is the Carr-Purcell-Meiboom-Gill (CPMG) method of measuring transverse (spin-spin) relaxation time ($T_2$). CPMG involves applying a series of radio-frequency (RF) pulses that tip the nuclear spins in a directional orthogonal to the equilibrium state and then uses a refocusing pulse to create successive echoes (with echo spacing $T_e$) that reveal the magnetization decay as a function of time M(t). In the simplest case of a sample containing only one molecular species, this decay of magnetization can be analyzed as a single component having an exponential decay in time t; $M(t)=M_0 e^{-t/T_2}$. In other cases where a sample contains multiple chemical components, the decay will be multi-exponential, having multiple (n), different $T_2$ components; $M(t)=\Sigma_i^n M_{0,i} e^{-t/T_{2,i}}$.

Other frequently utilized NMR techniques involve the determination of the longitudinal (spin-lattice) relaxation time $T_1$ of a sample, and the determination of NMR diffusion D. Tools for conducting NMR experiments are well-known. An NMR borehole tool for making NMR measurements of NMR parameters such as relaxation times and diffusion coefficients of fluids is described in Freedman, R. et al., "A compact high-performance low-field NMR apparatus for measurements on fluids at very high pressures and temperatures", Rev. Sci. Instrum. 85, 025102 (2014) which is hereby incorporated by reference in its entirety herein.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Methods and systems are provided for identifying one or more transition characteristics in a hydrocarbon fluid. A transition characteristic is determined by subjecting the fluid to different pressures or temperatures, conducting NMR tests at the different pressures or temperatures to obtain data, processing the data to obtain a signature of a function of the NMR parameter as a function of pressure or temperature, and analyzing the signature to find the transition characteristic.

In some examples, a transition characteristic that is determined is the asphaltene onset pressure (AOP) of a fluid. In some examples, the transition characteristic that is determined is a bubble point of the fluid. In some examples, the transition characteristic that is determined is the dew point of the fluid. In some examples, the transition characteristic that is determined is a wax dropout pressure.

In some examples, the function of an NMR parameter that is analyzed is a function of the $T_2$ of the sample. In some examples, the $T_2$ function is a linear mean (first moment) of $T_2$, $<T_2>$, as a function of pressure or temperature. In some examples, the $T_2$ function is a logarithmic mean of $T_2$, $T_{2LM}$, as a function of pressure or temperature. In some examples, the $T_2$ function is linear mean of the square of $T_2$ divided by the linear mean of $T_2$, $<T_2^2>/<T_2>$, as a function of pressure or temperature. In some examples, the function of the NMR parameter that is analyzed is a function of the diffusion D of the sample as a function of pressure or temperature. In some examples, the function of the NMR parameter that is analyzed is the initial magnetization $M_0$ of the fluid sample as a function of pressure or temperature. In some examples, the function of the NMR parameter that is analyzed is the $T_1$-$T_2$ ratio as a function of pressure or temperature. In some examples, the function of the NMR parameter that is analyzed is the D–$T_2$ ratio as a function of pressure or temperature. In some examples, the function of the NMR parameter that is analyzed is the shape of the $T_2$ distribution as a function of pressure or temperature.

In some examples, an AOP of a fluid sample is determined by subjecting the fluid sample to a pressure, conducting an NMR experiment on the fluid sample in order to find a function of the $T_2$ distribution of the sample at that pressure, repeatedly reducing the pressure on the sample and repeatedly conducting the NMR experiment at the different pressures, and analyzing the resulting data to express the data as a function of the $T_2$ distribution of the sample as a function of pressure to find a discontinuity, where the pressure at the discontinuity is taken as the AOP. In some examples, the discontinuity is found by conducting a dual linear fit of the data. In some examples, the discontinuity is found by conducting instantaneous slope calculations. In some examples, the discontinuity is found using a Bayesian change point algorithm.

In some examples, a system for determining a property of a substance includes an NMR system for applying NMR pulse sequences to a substance and detecting NMR signals generated by the substance to obtain NMR signal data, a processor; and a memory storing instructions executable by the processor to perform processes. The processes include subjecting the substance at multiple pressures or temperatures to magnetic fields and obtaining the NMR signals, processing the NMR signals to generate a signature of a function of an NMR parameter as a function of pressure or temperature; and identifying a fluid transition characteristic of the substance by locating a discontinuity in the signature.

Additional aspects and examples may be understood with reference to the following detailed description taken in conjunction with the provided drawings.

DETAILED DESCRIPTION

The particulars shown herein are by way of example and for purposes of illustrative discussion of the examples of the subject disclosure, and should not be considered limiting to the subject matter of the present disclosure. Furthermore, like reference numbers and designations in the various drawings indicate like elements unless indicated otherwise.

In one aspect, and as will be described in detail hereinafter, a discontinuity in the signature of one or more NMR parameters as a function of pressure or temperature may be used to identify a transition characteristic of the fluid such as the asphaltene onset pressure (AOP), bubble point, dew point, wax dropout pressure, and/or other transition characteristics of the fluid. For purposes herein, the term "transition characteristic" should be understood broadly to encompass actual and apparent changes in phase of the fluid. Thus, the AOP is the transition characteristic when components of asphaltenes that are in suspension in the fluid drop out. For a given temperature, the AOP of a fluid is a characteristic pressure at and below which asphaltene flocculates form. The bubble point is the transition characteristic that identifies gas coming out of solution. Again, for a given temperature, the bubble point of a fluid is a characteristic pressure at and below which phase separation from a single liquid phase to two phases (gas and liquid) occurs. The dew point is the transition characteristic when a gas condenses into a liquid. For a given temperature, the dew point of a fluid is a characteristic pressure at and below which phase separation from a single gaseous phase to two phases (gas and liquid) occurs. It should be appreciated that while each transition characteristic may be described as a transition that occurs with respect to a change of pressure at a given temperature, the transition characteristic may also be described as a transition that occurs with respect to a change of temperature at a given pressure. For purposes of brevity, however, examples may be described herein mostly with respect to change of pressure at a given temperature.

Depressurization of a crude oil causes changes in the NMR signature (i.e., a plot of an NMR parameter) of that oil. For instance, initial magnetization will decrease due to decreased proton density. Additionally, a phase change or transition, such as the aggregation of dispersed particulates, will also affect the NMR signature, and according to one aspect are seen to result in a discontinuity in the NMR signature that can be located and identified with the phase change or transition. In this regard, NMR measurements of relaxation and diffusion are a sensitive probe of the molecular dynamics in a fluid. When the fluid undergoes a phase change or transition such as asphaltene drop-out or gas bubbling or dew forming, the molecular dynamics change. In one aspect, a measurement of NMR parameters is able to detect a phase change or transition such as asphaltene drop-out, gas bubbling and dew forming. In principle, any relaxation or diffusion parameter such as $T_1$, $T_2$ and D, including multi-dimensional variants involving two or more relaxation or diffusion parameters such as $T_1$-$T_2$, $T_2$-D, etc., is capable of detecting changes in the molecular dynamics.

In one embodiment, an NMR system was used to detect AOP of an oil (fluid) sample by detecting significant changes in functions of the $T_2$ parameter of the fluid as a function of pressure. The AOP was corroborated by optical experiments that were done in tandem with the NMR system analysis. Thus, a low-field NMR system such as described in Freedman, R. et al., "A compact high-performance low-field NMR apparatus for measurements on fluids at very high pressures and temperatures", Rev. Sci. Instrum. 85, 025102 (2014) was utilized to conduct NMR tests such as CPMG experiments that measure transverse relaxation times $T_2$. In particular, three experimental runs were performed on two oils that were previously included in a live oil NMR database. "Oil 9" is known to have 0.8% by weight asphaltene as determined by the well-known SARA (Saturates, Asphaltenes, Resins and Aromatics) analysis, and the NMR testing was run at 125° C. and 175° C. "Oil 19" is similarly known to have 5.1% by weight asphaltene and NMR testing was run at 125° C. For each test, the live oil was brought to the identified temperature and was pressurized to 15 kpsi. A full suite of CPMG, $T_1$-$T_2$ and pulse-field gradient (PFG) CPMG (capable of determining NMR diffusion D) experiments were run at the initial pressure, and then the pressure was lowered by 100 psi/minute in steps of 1-2 kpsi. CPMG measurements were taken at each pressure step and during depressurization to provide a $T_2$ signature. Pressure steps were decreased to 200 psi near the expected AOP and continued until 500-1000 psi below the expected AOP, where a second set of the full suite of CPMG, $T_1$-$T_2$ and PFG experiments were performed. The pressure was then again lowed in increments while CPMG data was taken. Optical measurements were also taken using a Cary FT-NIR spectrometer measuring wavelengths in the range of 400-2000 nm. The absorption spectrum at 1500 nm was used to verify AOP as that wavelength is typically spectrally inactive and is routinely used to detect AOP using distributed Bragg reflector (DBR) lasers since any change at that wavelength is therefore a measure of scattering. Additionally, the AOP for Oil 9 was measured by High Pressure Microscopy, while the AOP for Oil 19 had been previously measured by HPM and was expected to be approximately 7000 psi at 125° C.

To analyze the data, the data were processed using a processor, and different functions of $T_2$ were calculated in addition to the initial magnetization, $M_0$. In particular, after an inverse Laplace Transform of the detected magnetization, M(t), a logarithmic mean of $T_2$ ($T_{2LM}$) was calculated. In addition, the initial magnetization $M_0$ and the average rate of decay $\langle 1/T_2 \rangle$ were calculated from a linear fit of the first twenty points in the CPMG decay with $M_0$ as the intercept of the fit and $\langle 1/T_2 \rangle$ as the slope of the line. Further, the linear average, or first moment of $T_2$ ($\langle T_2 \rangle$), was calculated directly from the CPMG data according to $\langle T_2 \rangle = \Sigma M(t)*t_e/M_0$, where $t_e$ is the CPMG echo time. A fourth function of $T_2$ calculated was the average of the square of $T_2$ divided by the average of $T_2$. This fourth function was calculated directly from the magnetization decay without the need for fitting according to $$\frac{\langle T_2^2 \rangle}{\langle T_2 \rangle} = \frac{\sum M(t)*t}{\sum M(t)}.$$

Figure 1:
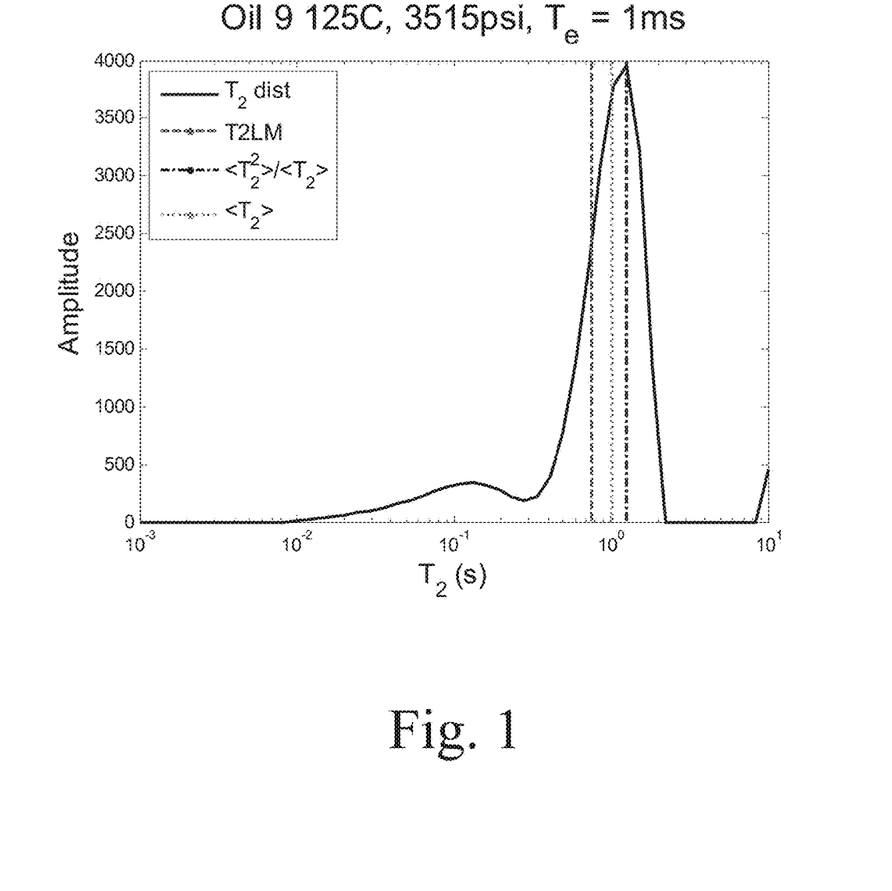
FIG. 1 is a plot of different $T_2$ function amplitudes for an oil at a particular pressure and temperature.

An illustration of the $T_2$ distribution as well as three of the functions of $T_2$ ($T_{2LM}$, $\langle T_2 \rangle$, and $$\left( T_{2LM}, \langle T_2 \rangle, \text{ and } \frac{\langle T_2^2 \rangle}{\langle T_2 \rangle} \right)$$

for Oil 9 at 125° C., a pressure of 3515 psi, and with $t_e$=1 ms is seen in FIG. 1. It is noted that all three functions are relatively close in value and that the function $$\frac{\langle T_2^2 \rangle}{\langle T_2 \rangle}$$

corresponds most closely with the peak of the $T_2$ distribution.

While it is not necessarily evident whether asphaltene drop-out would cause an increase, decrease, or no effect in $T_2$ after AOP or whether a change in $T_2$ after AOP would be significant enough to detect using NMR, the tests showed that $T_2$ increased significantly at AOP. In fact, as will be seen with reference to FIGS. 2-4, each of the three functions of $T_2$ shown in FIG. 1 can be useful in identifying the AOP of the oil. According to another aspect, other functions of $T_2$ and other functions of other NMR parameters can be useful in identifying the AOP (and other transition characteristics) of fluids.

Figure 2:
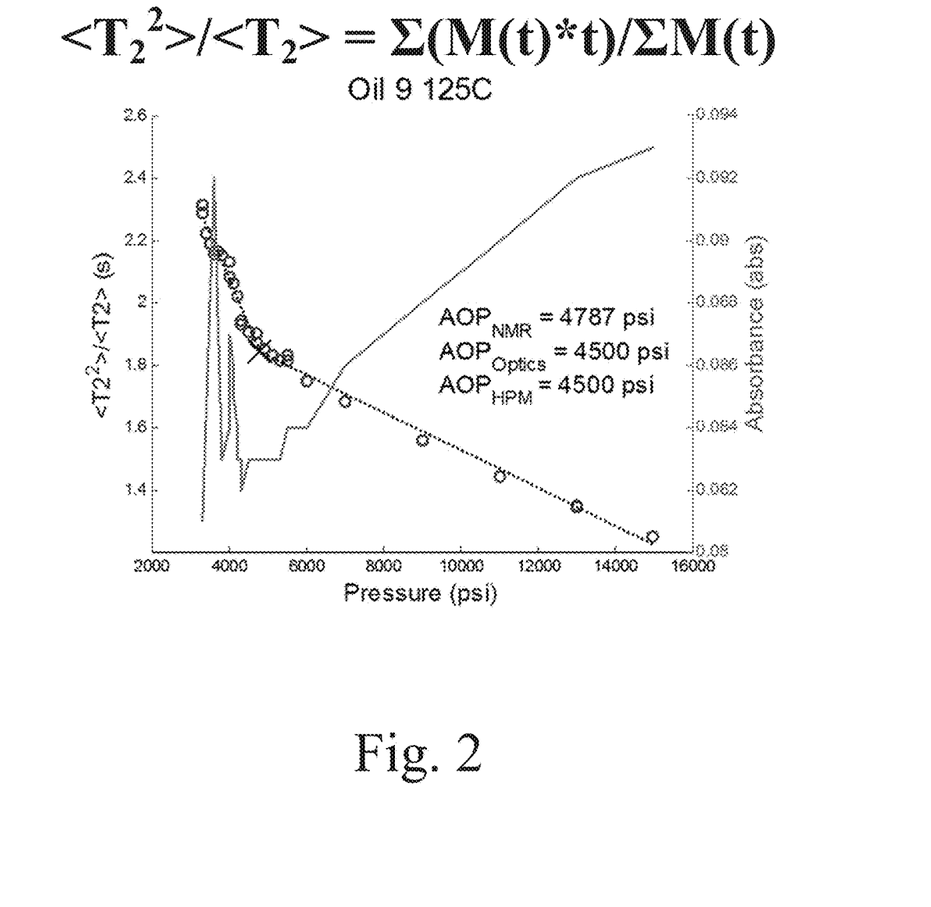
FIG. 2 is an AOP detection plot showing a first function of $T_2$ as a function of pressure and absorbance as a function of pressure for an oil at a particular temperature.

Turning now to FIG. 2, a function of $T_2$ is plotted as a function of pressure. More particularly, the average of the square of $T_2$ divided by the average of $$T_2 \left( \frac{\langle T_2^2 \rangle}{\langle T_2 \rangle} \right)$$

is plotted for Oil 9 at 175° C. as a function of pressure. Also plotted is the absorbance as a function of pressure as measured by the optical equipment. The generated data points for the NMR function were subjected to a dual linear fit, where the $T_2$ function values obtained at the ten highest pressures were fit to a first line, and the $T_2$ function values obtained at the eight lowest pressures were fit to a second line. More particularly, the coefficients of these lines were used to seed a non-linear least-squares fitting algorithm for the function T=max($B_1+M_1*P$, $B_2+M_2*P$), where $B_1$ and $B_2$ are the intercepts of the two lines, $M_1$ and $M_2$ are the slopes, T is the $T_2$ function, and P is the pressure. This fitting resulted in consistent determinations that gave an estimate of the AOP for the sample at the intersection of those lines (indicated by an "x") denoting a discontinuity, which in FIG. 2 is shown at 4787 psi. The AOP value estimated by this NMR technique was greater than the AOP pressure determined from the spectrometer (4300 psi) and less than the AOP value determined using HPM (5000 psi). It should be noted however, that the HPM measurement monitored continually mixed fluids, and mixing allows for more collisions that could result in flocculation which would therefore be more readily observed at higher pressures. In contrast, the NMR and optical measurements were made with fluids that were otherwise static. Thus, that the AOP measured by NMR was larger than the AOP measured by the optical measurement suggests that the NMR measurement may be more sensitive to subtle changes in the asphaltene flocculation than the optical measurement.

In another example, the dual-linear fit of the data may be seeded with lines best fit to the two extrama of the data both before and after the AOP. A simple dual-linear fit seeded with the lines best fit to the two extrama of the data gives a good approximation of AOP.

Figure 3:
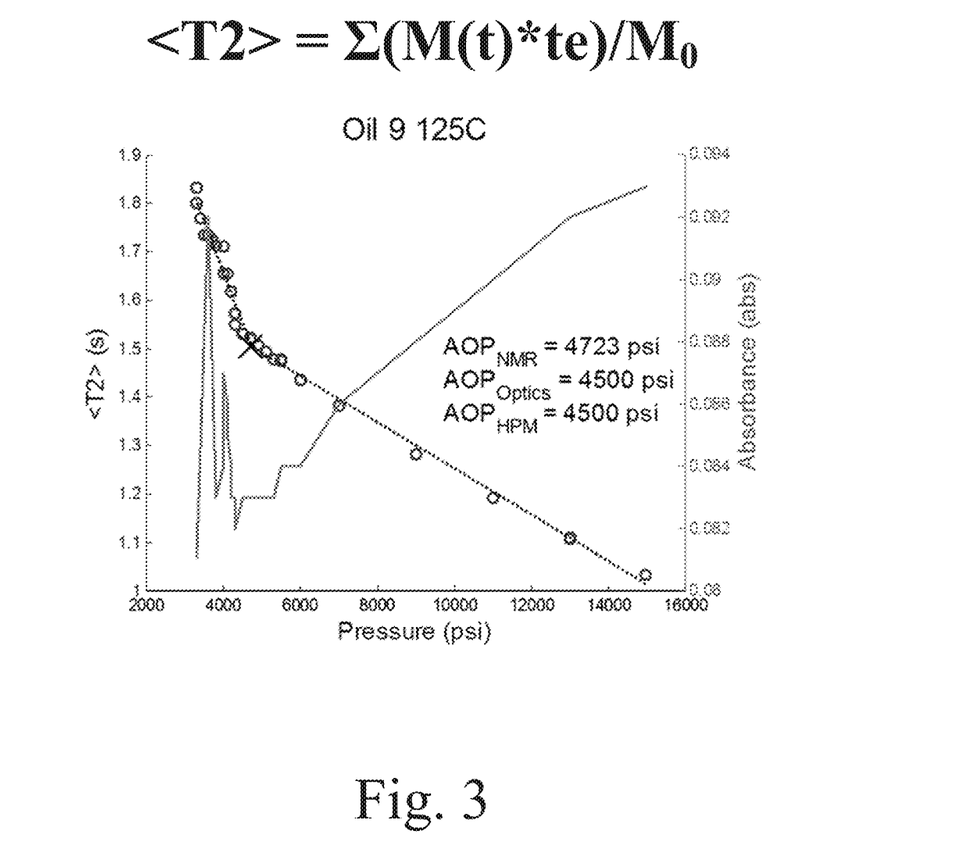
FIG. 3 is an AOP detection plot showing a second function of $T_2$ as a function of pressure and absorbance as a function of pressure for an oil at a particular temperature.
Figure 4:
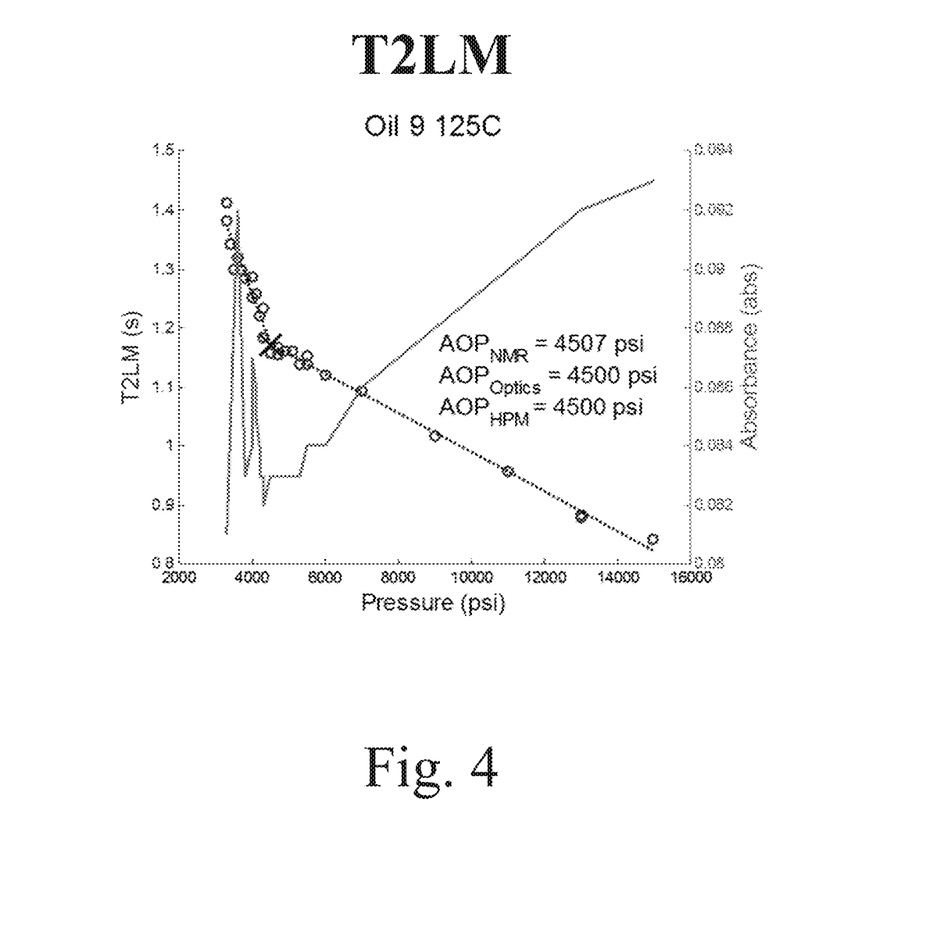
FIG. 4 is an AOP detection plot showing a third function of $T_2$ as a function of pressure and absorbance as a function of pressure for an oil at a particular temperature.

As previously mentioned, additional functions of $T_2$ were plotted as a function of pressure. In FIG. 3, a plot of the average or mean $T_2$ versus pressure is shown, whereas in FIG. 4, a plot of the logarithmic mean $T_2$ ($T_{2LM}$) is plotted as a function of pressure. Again, in each case, the generated data points for the NMR function were subjected to a dual linear fit, where the $T_2$ function values at higher pressures were fit to a first line and the $T_2$ function values at the lower pressures were fit to a second line and the coefficients of these lines were used to seed a non-linear least-squares fitting algorithm. The resulting AOP estimations were $AOP_{NMR}$=4723 psi for the mean $T_2$ function and $AOP_{NMR}$=4507 psi for the $T_{2LM}$ function, both of which are reasonably similar to the determination resulting from the $T_2$ function plotted in FIG. 2, and both of which are between the determinations obtained using the optical equipment and the HPM.

According to some examples, instead of utilizing a dual linear fit in order to find the discontinuity AOP point, a Bayesian change point detection (BOCPD) algorithm is utilized. See, e.g., "Adams, R. P., and MacKay D. J. C., "Bayesian Online Changepoint Detection", Technical report, University of Cambridge, Cambridge, UK (2007), arXiv:0710.3742v1. According to some examples, instead of utilizing a dual linear fit in order to find the discontinuity AOP point, the instantaneous slope of the $T_2$ function at adjacent pressure measurements is made, and the discontinuity point is identified when the instantaneous slope changes by a predetermined threshold value. If desired, even after a discontinuity point has been identified, one or more additional points may be analyzed to confirm that the identified discontinuity point is actually a discontinuity point in the plot. In some examples, two or more techniques such as dual linear fit, BOCPD and instantaneous slope are utilized to identify a discontinuity in the signature.

Figure 5:
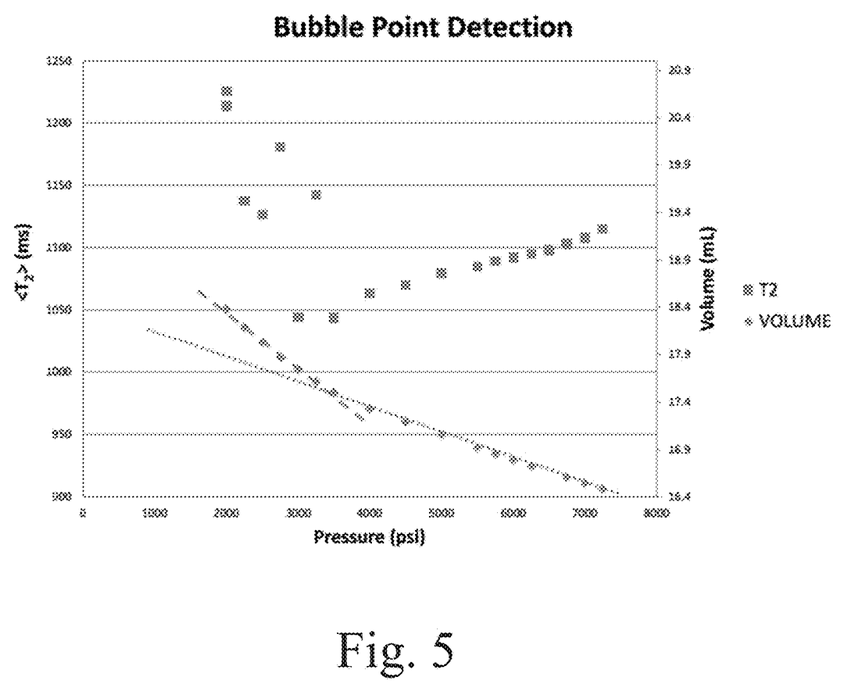
FIG. 5 is a bubble point detection plot showing a function of $T_2$ as a function of pressure and volume as a function of pressure for fluid comprised of dodecane and methane.

Turning now to FIG. 5, a bubble point detection plot is seen and includes NMR data, and volume data. More particularly, FIG. 5 is a plot that was obtained from subjecting a fluid mixture of dodecane and methane (approximately 50%-50% mole percentage) at 125° C. to an investigation similar to the investigation described above with reference to Oil 9, where a function of $T_2$ (i.e., the mean $T_2$) is plotted as a function of pressure (larger squares), and the volume of the sample is plotted as a function of pressure (smaller squares). From the volume data, it is seen that there is a discontinuity in the pressure-volume relationship at just below 3500 psi which is indicative of a bubble point at that pressure. Similarly, from the NMR data, it is seen that from about 7000 psi to about 3500 psi, the mean $T_2$ may be expressed as a linear function of pressure, but that at 3250 psi, the linear trend is broken. Thus, the discontinuity in the NMR data between 3500 psi and 3250 psi is indicative of a bubble point in that range. The discontinuity may be found using dual linear fitting, BOPCD, instantaneous slope calculation, or other techniques.

Figure 6:
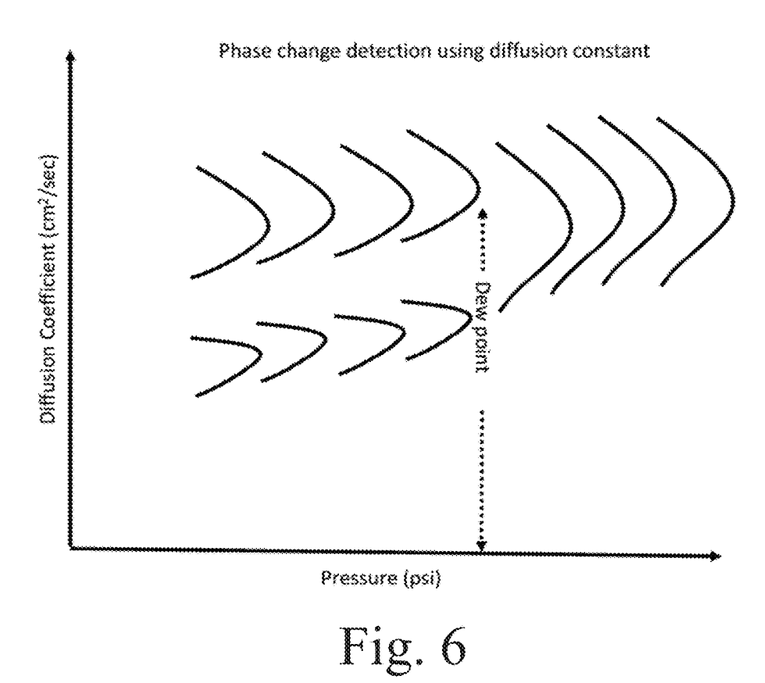
FIG. 6 is a hypothetical dew point detection plot showing NMR parameter D as a function of pressure for an oil at a particular temperature.

FIG. 6 is a hypothetical dew point detection plot showing NMR parameter D as a function of pressure for an oil at a particular temperature. More particularly, FIG. 6 shows expected diffusion coefficient distributions (curves) for eight different pressure values indicated by the "ticks" on the x axis. It is noted that the curves are amplitude curves and not pressure curves. For the curves representing the four highest pressure values, the diffusion coefficient distributions are indicative of a single mode distribution, whereas for the curves representing the four lower pressure values, the diffusion coefficient distributions are indicative of a bi-modal distribution. The dew point (i.e., where gas starts condensing into liquid) is taken at a point between the lowest of the four highest pressure values and the highest of the three lowest pressure values. It is noted that the diffusion coefficient distribution D itself is used in FIG. 6 as a function of pressure to find a discontinuity (the change from single mode to bi-modal) representing the dew point pressure. However, it may be stated that a function of the diffusion coefficient distribution D is used in FIG. 6 as a function of pressure to find discontinuity, as the diffusion coefficient distribution is a "function" of itself ("times one"). Other functions of the diffusion coefficient distribution as a function of pressure could be utilized.

In another embodiment, the function of the NMR parameter that is analyzed is the $D-T_2$ ratio as a function of pressure (or temperature). In another embodiment, the function of the NMR parameter that is analyzed is the shape of the $T_2$ distribution as a function of pressure (or temperature).

Figure 7:
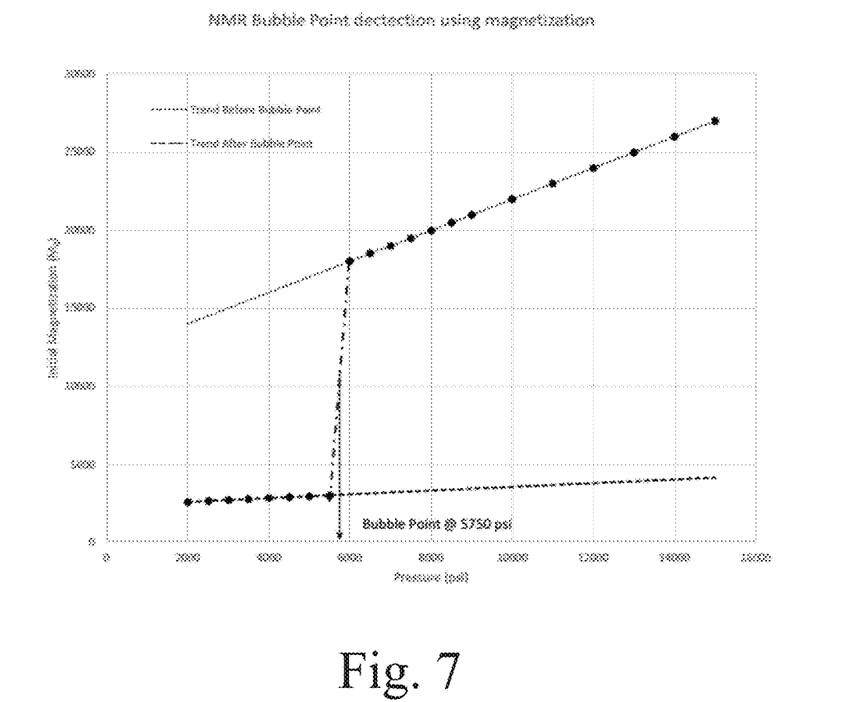
FIG. 7 is a hypothetical bubble point detection plot showing a function of initial magnetization $M_0$ as a function of pressure.

FIG. 7 is a hypothetical bubble point detection plot showing a function of initial magnetization $M_0$ as a function of pressure. FIG. 7 shows twenty-one determinations of $M_0$ plotted as a function of pressure from 15,000 psi down to 2000 psi. A discontinuity at between 6000 psi and 5500 psi is indicative of a bubble point therebetween (e.g., at about 5750 psi). The discontinuity is easily found using BOCPD. According to one aspect, dissolution of gas causes a significant decrease in the proton density of the sample (gas molecules occupy more space than the equivalent numbers of liquid molecules), making the discontinuity in $M_0$ an adequate indicator of bubble point. The dissolution of liquid from a gas (bubble point) or the flocculation of asphaletene molecules (AOP) within a liquid generally might not change the overall proton density significantly enough to be readily detectable as a change in $M_0$.

Figure 8:
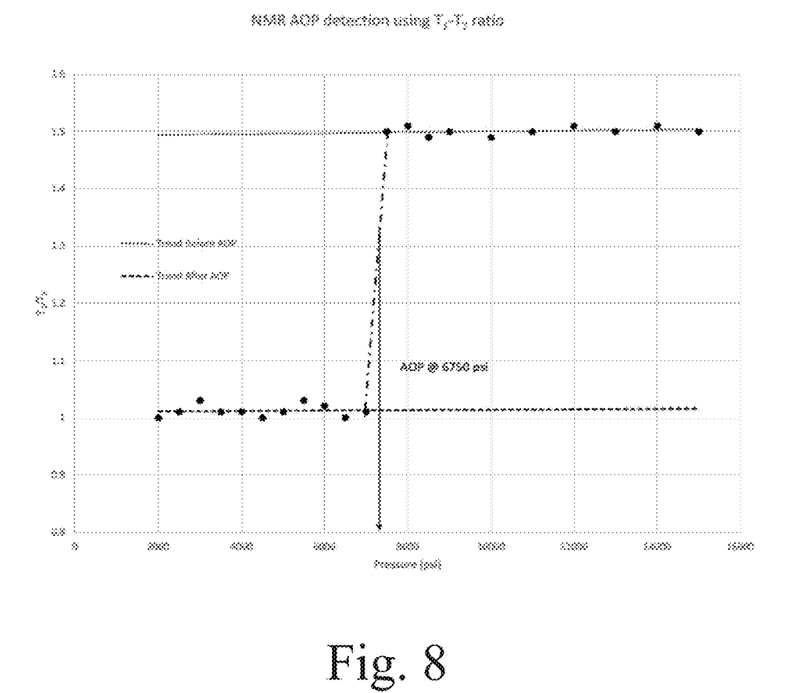
FIG. 8 is a hypothetical AOP detection plot showing the NMR $T_1$-$T_2$ ratio as a function of pressure.

FIG. 8 is a hypothetical AOP detection plot showing (a function of) the NMR $T_1-T_2$ ratio as a function of pressure. FIG. 8 shows the $T_1-T_2$ ratio plotted as a function of pressure from 15,000 psi down to 2000 psi. A discontinuity at between 7500 psi and 7000 psi is indicative of an AOP therebetween (e.g., at about 7250 psi). The discontinuity is easily found using BOCPD. It is understood that oils with unflocculated asphaltenes have a $T_1-T_2$ ratio that is significantly larger than the same oils with no asphaltene. When flocculates form and settle, the oil would be essentially free of asphaltene and the AOP could be determined using the $T_1-T_2$ ratio and examining for a point that creates a significant decrease of $T_1-T_2$ ratio. The same dynamics do not apply to phase changes (bubble point or dew point) as the $T_1-T_2$ ratio is generally unchanged during these transitions.

Figure 9:
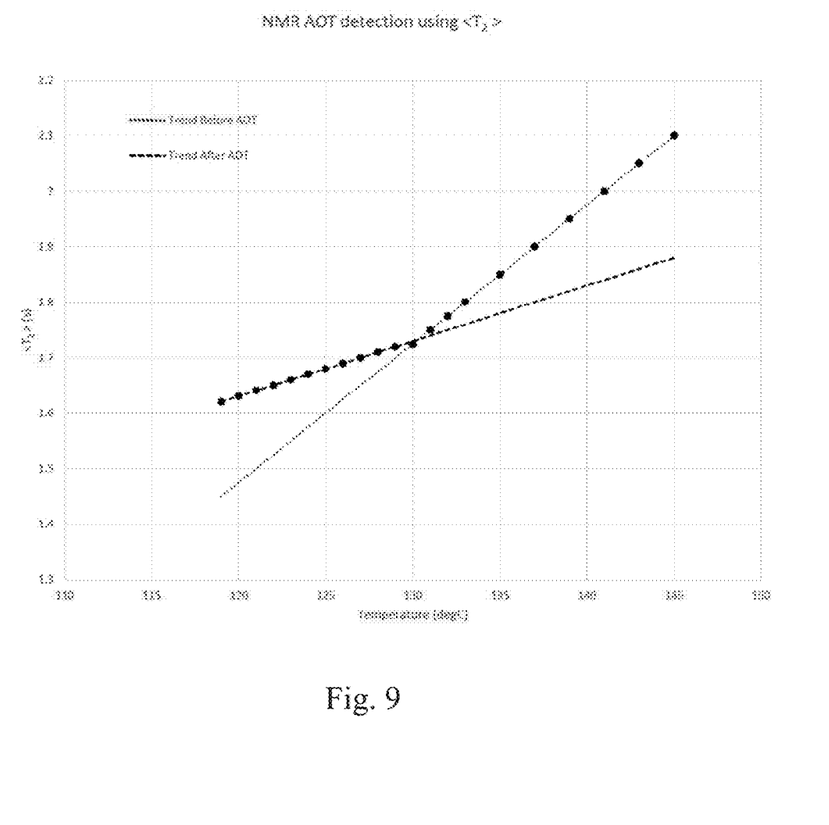
FIG. 9 is an asphaltene onset temperature (AOT) detection plot showing a function of $T_2$ as a function of temperature for an oil at a particular pressure.

FIG. 9 is a hypothetical asphaltene onset temperature (AOT) detection plot showing a function of $T_2$ as a function of temperature for an oil at a particular pressure. As seen in FIG. 9, a plot of the average or mean $T_2$ versus temperature is shown, with the generated data points for the NMR function being subjected to a dual linear fit, where the $T_2$ function values at higher temperatures were fit to a first line and the $T_2$ function values at the lower temperatures were fit to a second line. The junction (discontinuity) of these lines yields an AOT fluid transition characteristic of 130° C.

In some examples, the NMR equipment utilized to conduct experiments on a fluid of interest is located uphole, e.g., in a laboratory and with apparatus that is capable of applying and holding high pressure fluids and is further capable of changing the pressure and/or temperature of the fluids. Signals from the NMR equipment are provided to a processor associated with the NMR equipment that processes the signals in order to generate NMR parameter information which is a function of the pressure or temperature, and which are further processed to find a discontinuity that may be used to identify a transition characteristic of the fluid. A value for an estimate of the transition characteristic of the fluid may be output on a screen or on paper. Alternatively, or in addition, plots containing the transition characteristic estimate as determined from the NMR experiments (such as, e.g., FIGS. 2-9), may be output on a screen or on paper. The plots may or may not contain additional information such as optical plots (e.g., absorbance plotted as a function of pressure) or volume plots (e.g., volume plotted as a function of pressure).

In some examples, the NMR equipment utilized to conduct experiments is located downhole where oil sampled by a downhole sampling tool such as the MDT tool of Schlumberger Ltd. is passed into a pressure controlled chamber in the tool. The pressure (or temperature) in the chamber is then changed repeatedly or continuously as the NMR measurements are made. Signals from the NMR equipment are provided to a processor associated with the NMR equipment that may be located downhole and/or uphole and that processes the signals in order to generate NMR parameter information which is a function of the pressure or temperature. The NMR parameter information is further processed to find a discontinuity that may be used to identify a transition characteristic of the fluid. A value for an estimate of the transition characteristic of the fluid may be output on a screen or on paper. Alternatively, or in addition, plots containing the transition characteristic estimate as determined from the NMR experiments (such as, e.g., FIGS. 2-9), may be output on a screen or on paper. The plots may or may not contain additional information such as optical plots (e.g., absorbance plotted as a function of pressure) or volume plots (e.g., volume plotted as a function of pressure).

Figure 10:
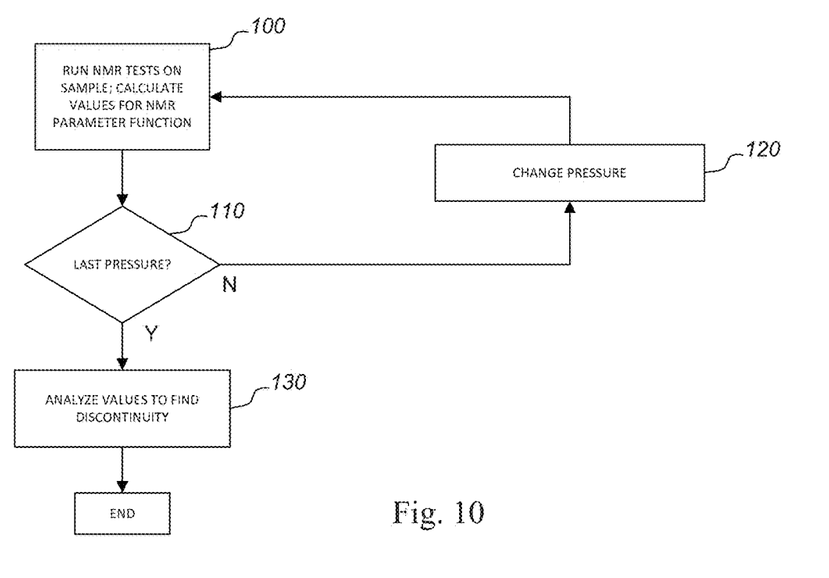
FIG. 10 is a flow chart of a method of an example implementation.

FIG. 10 is a flow chart of a method according to one embodiment. At 100, NMR tests are run on a fluid sample (i.e., the fluid sample is subjected to an NMR field) in order to obtain NMR signals, and the signals are processed in order to calculate a value for an NMR parameter function (e.g., a function of $T_2$) at a particular fluid sample pressure. At 110 a determination is made whether NMR tests have been made at all pressures of interest. If not, at 120, the pressure is changed (e.g., reduced), and the method continues at 100 where NMR tests are run at the new pressure in order to obtain signals which are processed in order to calculate a value for the NMR parameter function at the new sample pressure. This loop continues until a determination is made at 110 that all tests have been completed. Then, at 130, the values calculated at 100 are analyzed to find a discontinuity that may be used to identify a transition characteristic of the fluid. According to some examples, the analysis may employ a dual linear fit of data, a Bayesian change point detection algorithm, and/or a different analysis.

It will be appreciated with respect to the method of FIG. 10, instead of holding the temperature constant and changing the pressure, the pressure may be held constant and the temperature may be changed, and a discontinuity in the values of the NMR parameter function may be used to find a transition characteristic of the fluid.

Figure 11:
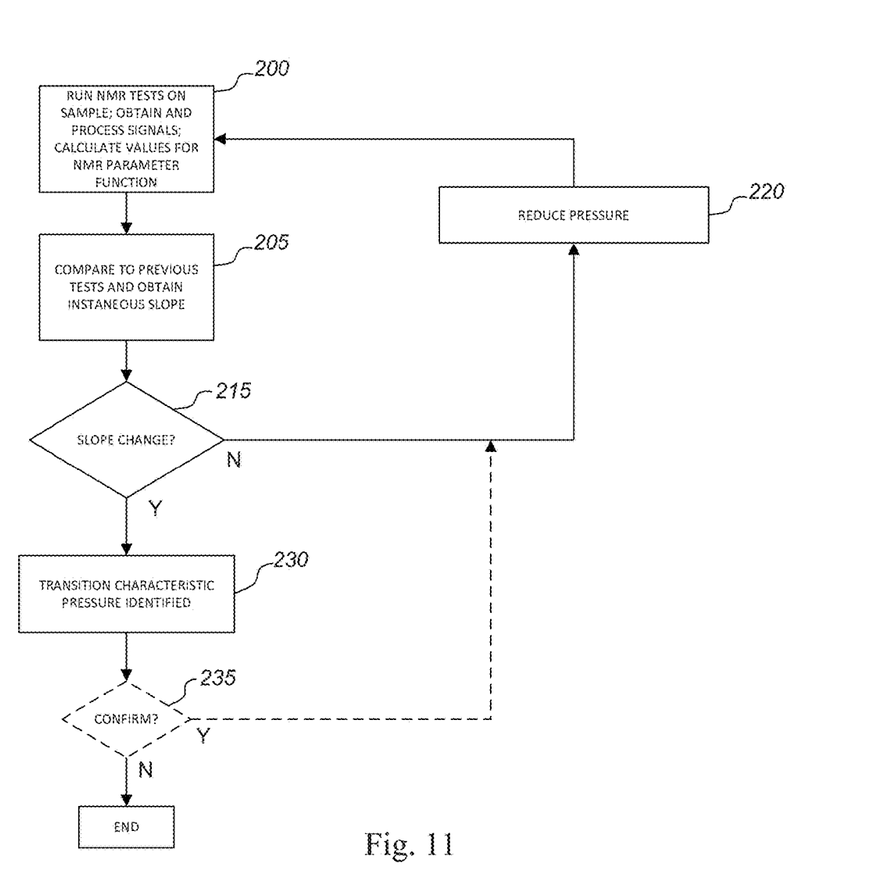
FIG. 11 is a flow chart of a method of an example implementation.

FIG. 11 is a flow chart of a method according to another embodiment. At 200, NMR tests are run on a fluid sample in order to obtain signals, and the signals are processed in order to calculate a value for an NMR parameter function (e.g., a function of $T_2$) at a particular fluid sample pressure. At 205, the results of the NMR tests are compared to previous tests and an instantaneous slope for the NMR parameter function as a function of pressure is calculated. At 215, the slope calculated at 205 is compared to a previous calculated slope to determine whether there has been a change in slope. If there is no change, at 220, the pressure is changed (e.g., reduced). The method then continues at 200 where NMR tests are run at the new pressure in order to obtain signals which are processed in order to calculate a value for the NMR pameter function at the new sample pressure, and at 205 where the results are compared to previous tests in order to calculate a new instantaneous slope, and at 215 where the new instantaneous slope is compared to a previous slope to determine whether has been a slope change. This loop continues until a determination is made that there has been a change in slope. The pressure at which the change in slope is found (or the previous pressure) is used at 230 to identify the pressure for the transition characteristic of the fluid. Optionally, after a change in slope is found at 215 additional confirmation tests 235 at at least one new pressure may be conducted to obtain signals which are processed in order to calculate a value for the NMR parameter function at the new sample pressure, and which can be used at 205 to calculate a new instantaneous slope that can be compared at 215 to the previous slope (or slopes previous to that) to confirm that the instantaneous slope has or has not changed from earlier slope determinations. If the slope change is confirmed, the identified pressure for the transition characteristic of the fluid is confirmed. If the slope change is not confirmed, the method may continue at 220, 200, 205, 215 . . . , until a slope change is confirmed.

Again, and with respect to, for example, the method of FIG. 11, it is noted that instead of changing the pressure at a particular temperature, the temperature may be changed at a given pressure and a discontinuity in the values in the NMR parameter function may be used to find a transition characteristic of the fluid.

In one aspect, some of the methods and processes described above, such as determining values of a function of an NMR parameter are performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCM-CIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

In one aspect, the methods described may be applied to geological formations downhole, on uphole on fluid samples. Where the methods are carried out with downhole NMR tools, the processing of the obtained signals may be carried out downhole and/or uphole.

As used in the description and claims of the present application, the phrase "at least one of" followed by recitation of plurality of features should be considered disjunctive rather than conjunctive. For example, a recitation of "at least one of a first element and a second element" should be construed to refer to the first element alone, the second element alone, or the first and second elements in combination.

Although several examples have been described in detail above, those skilled in the art will readily appreciate that many modifications are possible without materially departing from this subject disclosure. Thus, by way of example only, and not by way of limitation, while various embodiments describe pressures or temperatures on a sample being reduced in a step fashion, the pressure or temperature changes need not be done in a step fashion, can be continuous, can be increased rather than reduced, or can be changed with both increases and reductions in any sequence. Also, while particular functions of a NMR parameters were described such as the mean value, the logarithmic mean, etc., other functions could be utilized. Accordingly, all such modifications are intended to be included within the scope of this disclosure as defined in the following claims. It is the express intention of the applicant not to invoke 35 U.S.C. § 112, paragraph 6 for any limitations of any of the claims herein, except for those in which the claim expressly uses the words 'means for' together with an associated function.

The invention claimed is:

1. A method of identifying a hydrocarbon fluid transition characteristic of a fluid sample, comprising:
  subjecting the fluid sample at multiple pressures or temperatures to magnetic fields and obtaining nuclear magnetic resonance (NMR) signals;

processing the NMR signals to generate a signature of a function of an NMR parameter as a function of pressure or temperature; and
identifying a fluid transition characteristic of the sample by locating a discontinuity in the signature.

2. The method according to claim 1, wherein:
the fluid transition characteristic is one of an asphaltene onset pressure (AOP) of the fluid sample, a bubble point of the fluid sample, and a dew point of the fluid sample.

3. The method according to claim 1, wherein:
the NMR parameter is one of a relaxation parameter, a diffusion parameter and an initial magnetization parameter, or a combination thereof.

4. The method according to claim 3, wherein:
the NMR parameter is the transverse relaxation time ($T_2$).

5. The method according to claim 4, wherein:
the function of the NMR parameter is one of a linear mean of $T_2$, a logarithmic mean of $T_2$, and a linear mean of the square of $T_2$ divided by the linear mean of $T_2$.

6. The method according to claim 5, wherein:
the locating a discontinuity comprises fitting the signature to two lines using a dual linear fit.

7. The method according to claim 5, wherein:
the locating a discontinuity comprises utilizing a Bayesian change point detection (BOCPD) algorithm on data of the signature.

8. The method according to claim 5, wherein:
the locating a discontinuity comprises repeatedly calculating instantaneous slopes of the signature.

9. The method according to claim 3, wherein:
the NMR parameter is a ratio of a longitudinal relaxation time $T_1$ and a transverse relaxation time $T_2$.

10. The method according to claim 3, wherein:
the NMR parameter is the diffusion parameter.

11. The method according to claim 10, wherein:
the function of the NMR parameter is a diffusion coefficient D distribution.

12. The method according to claim 3, wherein:
the NMR parameter is a combination of the diffusion parameter and the relaxation parameter.

13. The method according to claim 12, wherein:
the function of the NMR parameter is a ratio of a diffusion coefficient D and a transverse relaxation time $T_2$.

14. The method according to claim 3, wherein:
the NMR parameter is the initial magnetization parameter $M_0$.

15. The method according to claim 1, wherein:
the locating a discontinuity comprises fitting the signature to two lines using a dual linear fit.

16. The method according to claim 1, wherein:
the locating a discontinuity comprises utilizing a Bayesian change point detection (BOCPD) algorithm on data of the signature.

17. The method according to claim 1, wherein:
the locating a discontinuity comprises repeatedly calculating instantaneous slopes of the signature.

18. The method according to claim 1, further comprising:
displaying the signature.

19. A method of identifying the asphaltene onset pressure (AOP) of a fluid sample, comprising:
repeatedly subjecting the fluid sample at different pressures or temperatures to magnetic fields and obtaining nuclear magnetic resonance (NMR) signals;
processing the NMR signals to obtain values of a function of an NMR parameter as a function of pressure or temperature;
analyzing the values to locate a discontinuity in a pattern of the values; and
identifying the AOP as the pressure of the discontinuity.

20. A method according to claim 19, further comprising:
displaying the values of a function of an NMR parameter as a function of pressure or temperature.

21. The method according to claim 19, wherein:
the function of the NMR parameter is one of a linear mean of $T_2$, a logarithmic mean of $T_2$, and a linear mean of the square of $T_2$ divided by the linear mean of $T_2$.

22. The method according to claim 19, wherein:
the analyzing the values comprises fitting the values to two lines using a dual linear fit, and
the identifying comprises finding an intersection of the two lines, wherein the intersection comprises the discontinuity.

23. The method according to claim 19, wherein:
the repeatedly subjecting the fluid sample at different pressures or temperatures comprises subjecting the fluid sample to a first pressure or temperature and applying the NMR fields, and repeatedly reducing pressure or changing temperature on the fluid sample and applying the NMR fields.

24. A system for determining a property of a substance, the system comprising:
a nuclear magnetic resonance (NMR) system for applying NMR pulse sequences to a substance and detecting NMR signals generated by the substance to obtain NMR signal data;
a processor; and
a memory storing instructions executable by the processor to perform processes that include:
subjecting the substance at multiple pressures or temperatures to magnetic fields and obtaining the NMR signals;
processing the NMR signals to generate a signature of a function of an NMR parameter as a function of pressure or temperature; and
identifying a fluid transition characteristic of the substance by locating a discontinuity in the signature.

* * * * *